United States Patent [19]

DeMarinis et al.

[11] 4,059,578
[45] Nov. 22, 1977

[54] 7-SUBSTITUTED MERCAPTOACETAMIDO CEPHAMYCINS

[75] Inventors: Robert M. DeMarinis, King of Prussia, Pa.; Jerry A. Weisbach, Cherry Hill, N.J.

[73] Assignee: SmithKline Corporation, Philadelphia, Pa.

[21] Appl. No.: 540,482

[22] Filed: Jan. 13, 1975

Related U.S. Application Data

[63] Continuation-in-part of Ser. No. 504,619, Sept. 9, 1974, abandoned.

[51] Int. Cl.$^2$ ................ C07D 501/50; A61K 31/545
[52] U.S. Cl. ........................................ 544/21; 424/246
[58] Field of Search ....................... 260/243 C; 424/246

[56] References Cited

U.S. PATENT DOCUMENTS

| 3,859,282 | 1/1975 | Cheng et al. | 260/243 C |
| 3,883,520 | 5/1975 | DeMarinis | 260/243 C |
| 3,884,915 | 5/1975 | DeMarinis | 260/243 C |
| 3,887,549 | 6/1975 | Christensen | 260/243 C |
| 3,920,639 | 11/1975 | Dolfini | 260/243 C |
| 3,960,845 | 6/1976 | Hiraoka et al. | 260/239.1 |
| 4,007,177 | 2/1977 | Nakao et al. | 260/243 C |

FOREIGN PATENT DOCUMENTS

| 2,455,884 | 5/1975 | Germany |
| 1,023,285 | 2/1976 | Japan |

*Primary Examiner*—Nicholas S. Rizzo
*Assistant Examiner*—Diana G. Rivers
*Attorney, Agent, or Firm*—Stuart R. Suter; William H. Edgerton; Alan D. Lourie

[57] ABSTRACT

7β-Substituted mercaptoacetamido-7α-methoxycephalosporanic acid and derivatives thereof are prepared. These compounds are antibacterial agents with improved properties.

10 Claims, No Drawings

7-SUBSTITUTED MERCAPTOACETAMIDO CEPHAMYCINS

This is a continuation-in-part of copending application Ser. No. 504,619, filed Sept. 9, 1974, now abandoned.

This invention relates to new cephalosporins and particularly to new compounds in the cephamycin series which have antibacterial properties.

BACKGROUND

A new series of natural cephalosporins have recently been reported and given the class name of cephamycin. The distinguishing feature of this class of cephalosporins is the 7α-methoxy group. Two naturally-occurring cephamycins have been reported by Nagarajan et al., *J. Amer. Chem. Soc.*, 93, 2308 (1971). These compounds have the cephalosporin C acyl group at position 7 and acetoxymethyl or carbamoyloxymethyl at position 3. These compounds and others which have been modified at position 3 are disclosed in Belgian Pat. No. 764,160 (Farmdoc 61445S) and Netherlands Pat. No. 7103135 (Farmdoc 62434S).

Compounds with other acyl groups have been disclosed. For example, 7-methoxycephalothin is reported in Netherlands patent No. 7304755 (Farmdoc 66543U) and *J. Amer. Chem. Soc.*, 94, 1408 (1972). The same patent also discloses 7α-methoxy-7β-thienylacetamido-3-carbamoyloxy-3-cephem-4-carboxylic acid. South African Pat. No. 71 3229 discloses compounds and process for preparing them with various acyl groups.

DESCRIPTION OF THE INVENTION

The compounds of this invention are defined by the following structural formula:

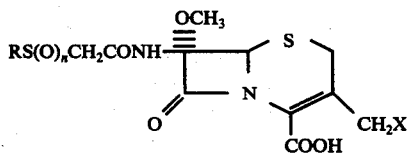

wherein:
R is $CF_3$, $CF_3CH_2$, lower alkyl of 1–4 carbon atoms, or $NCCH_2$;
n is 0, 1 or 2;
X is acetoxy or SHet; and
Het is tetrazolyl, triazolyl, thiadiazolyl or oxadidiazolyl each unsubstituted or substituted with 1 or 2 alkyl groups of 1–4 carbon atoms.

Herein the term lower alkyl means alkyl groups containing one to four carbon atoms.

Preferred acyl groups at position 7 are trifluoromethylmercaptoacetyl, trifluoromethylsulfinylacetyl, trifluoromethylsulfonylacetyl, trifluoroethylmercaptoacetyl, trifluoroethylsulfinylacetyl, cyanomethylmercaptoacetyl, cyanomethylsulfinylacetyl, cyanomethylsulfonylacetyl, methylmercaptoacetyl, methylsulfinylacetyl, and methylsulfonylacetyl.

Particular preferred acyl groups are trifluoromethylmercaptoacetyl, trifluoroethylsulfinylacetyl, cyanomethylmercaptoacetyl, cyanomethylsulfinylacetyl, methylsulfonylacetyl, and methylmercaptoacetyl.

Preferred substituents at position 3 are those where X is acetoxy or SHet and Het is tetrazolyl, 1,2,3-triazolyl, 1,2,4-triazolyl, 1,3,4-thiadiazolyl, or 1,3,4-oxadiazolyl, each optionally substituted with methyl groups. The methyl substituents may be 1 or 2 in number and bonded to carbon or a hetero atom.

Particularly preferred substituents at position 3 are those where X is acetoxy or 1-methyltetrazol-5-ylthio.

Due to the carboxylic acid group, the compounds of this invention will form salts with bases. These salts are also within the scope of this invention. The salts are prepared by standard methods using a variety of bases containing nontoxic pharmaceutically acceptable cations such as alkali metal, alkaline earth, or ammonium cations.

The compounds of this invention are prepared by acylation of the appropriate 7β-amino-7α-methoxycephalosporin nucleus with an appropriate acetic acid. The acetic acid derivative is activated for acylation by any of the standard methods known and used in the art such as mixed anhydride, acid chloride, or activated ester. In addition, a coupling reagent, for example dicyclohexylcarbodiimide, can be used provided that the carboxyl group on the cephem nucleus is protected with an easily removable protecting group. Ester protecting groups are well known in the art and include for example t-butyl, trichloroethyl, benzhydryl, benzoxymethyl, benzyl, 4-methoxyphenyl, 4-methoxybenzyl, 4-nitrophenyl or 4-nitrobenzyl.

Alternatively, the compounds where X is SHet can be prepared by displacing the acetoxy group of 7α-methoxy-7β-substituted acetamidocephalosporanic acid, which is prepared as described above, with the appropriate heterocyclicthiol.

The starting materials are known in the art, prepared by analogous methods, or described herein. The 7β-amino-7α-methoxycephem nuclei are prepared from the corresponding 7β-aminocephem nuclei by methods analogous to those disclosed in *J. Org. Chem.*, 38, 2857 (1973) or Belgian Pat. No. 794,554 (Farmdoc 46690U). Trifluoromethylmercaptoacetic acid is prepared by methods disclosed in U.S. Pat. No. 3,828,037. Trifluoromethylsulfinylacetic acid is prepared by oxidation of trifluoromethylmercaptoacetic acid by the procedure disclosed in *Zh. Obshch. Khim*, 35, 1628 (1965). The alkylmercaptoacetic acids are prepared by standard methods by reacting an alkylmercaptan with bromoacetic acid in the presence of base. These alkylmercaptoacetic acids or an ester thereof are oxidized by known methods with one or two equivalents of an oxidation reagent such as m-chloroperbenzoic acid, to give the alkylsulfinyl and alkylsulfonyl derivatives. The acetic acid derivatives where R is cyanomethyl or trifluoroethyl are prepared in analogous manner to the above alkyl derivative.

The compounds of this invention have antibacterial activity against both Gram-positive and Gram-negative organisms. These compounds are particularly useful since they are effective against some organisms which are generally resistant to cephalosporins such as Proteus, Serratia, Enterobacter and Pseudomonas. Minimum inhibitory concentrations (MIC) were determined using the standard tube dilution method described in *Antib. Chemother.*, 9, 307 (1950). 7α-Methoxy-7β-trifluoromethylmercaptoacetamido-3-(1-methyltetrazol-5-ylthiomethyl)-3-cephem-4-carboxylic acid had MIC's ranging from 0.8 to greater than 200 µg/ml when tested against a variety of bacteria. In addition, the compounds are advantageous in that they exhibit higher and more prolonged blood levels than related compounds.

The compounds are formulated into pharmaceutical compositions in the same manner as other known cephalosporins and is within the ability of one skilled in the art. They are administered parenterally as sterile aqueous solutions or orally as capsules, tablets, suspensions and the like to prevent or treat bacterial infections. The dosage varies with the age, size and condition of the subject as well as the severity of the infection. Daily dosage ranges from 1 to 5 grams which may be given in divided amounts, usually 2 to 6 doses per day.

The following examples are presented to illustrate the invention but are not to be construed as limiting the scope thereof.

PREPARATION 1

A suspension of t-butyl 7-amino-3-(1-methyltetrazol-5-ylthiomethyl)-3-cephem-4-carboxylate (11.5 g, 0.03 mol) and methanol (225 ml) was stirred and warmed until a cloudy suspension remained. To this mixture was added benzaldehyde (3.71 g, 0.035 mol) in a small amount of methanol. The solution was stirred for 15 minutes and then cooled to 0°. The precipitate was filtered, washed with methanol and dried.

The above imine (8.5 g, 18 mmol) in tetrahydrofuran (100 ml) was cooled to −70° and treated with 1.8M phenyl lithium solution (11 ml, 19.8 mmol). The mixture was stirred for 15 minutes and then methyl methanethiosulfonate (2.52 g, 20 mmol) in tetrahydrofuran (10 ml) was added. The reaction was stirred in the cold for one hour and then treated with acetic acid (1.5 ml) in tetrahydrofuran (5 ml). The solution was poured into water (200 ml) and extracted with ethyl acetate (500 ml). The extracts were washed with water, 5% $NaHCO_3$, water and saturated sodium chloride, dried and evaporated to the 7α-methylthio derivative, which was chromatographed on silica gel with benzene as eluant.

The 7α-methylthio derivative (1.09 g, 2.0 mmol) was dissolved in acetone (20 ml) and treated with p-toluenesulfonic acid (400 mg) in acetone (5 ml) at room temperature for 30 minutes. The solution was evaporated to about 5 ml and ether was added until the solution was cloudy. Upon cooling, crystals of the salt formed which were collected and dried. The salt was suspended in chloroform (100 ml) and stirred with 5% $Na_2CO_3$. The organic phase was dried and evaporated to about 2 ml. Ether was added and the resulting solution was cooled until crystals of the 7β-amino-7α-methylthiocephem derivative was formed.

The above product (473 mg) was dissolved in methanol (25 ml) and dry dimethylformamide (10 ml) and cooled to −15°. Dry pyridine (0.275 g) was added followed by $HgCl_2$ (725 mg). The mixture was stirred for 15 minutes and the solid precipitate was filtered. The filtrate was diluted with ether and extracted with water. The organic phase was dried and evaporated to give t-butyl 7β-amino-7α-methoxy-3-(1-methyltetrazol-5-ylthiomethyl)-3-cephem-4-carboxylate.

PREPARATION 2

When the appropriate 7-aminocephem nucleus is substituted into the procedure of Preparation 1, the following compounds are obtained:

t-butyl 7β-amino-7α-methoxycephalosporanate
t-butyl 7β-amino-7α-methoxy-3-(5-methyl-1,3,4-thiadiazol-2-ylthiomethyl)-3-cephem-4-carboxylate
t-butyl 7β-amino-7α-methoxy-3-(5-methyl-1,3,4-oxadiazol-2-ylthiomethyl)-3-cephem-4-carboxylate
t-butyl 7β-amino-7α-methoxy-3-(1-methyl-1,2,3-triazol-5-ylthiomethyl)-3-cephem-4-carboxylate
t-butyl 7β-amino-7α-methoxy-3-(4-methyl-1,2,4-triazol-3-ylthiomethyl)-3-cephem-4-carboxylate
t-butyl 7β-amino-7α-methoxy-3-(4,5-dimethyl-1,2,4-triazol-3-ylthiomethyl)-3-cephem-4-carboxylate.

PREPARATION 3

A solution of dry methanol (1.12 g, 35 mmol) in dry tetrahydrofuran (200 ml) is cooled to −20° and treated with 2.1M n-butyl lithium (16.7 g). This solution is cooled to −68° and a solution of t-butyl 7-(p-nitrobenzyloxycarbonylamino)cephalosporanate (5.09 g, 10 mmol) in dry tetrahydrofuran (50 ml) is added over a 10 minute period. The solution is stirred rapidly while t-butyl hypochlorite (1.08 g, 10 mmol) is added. The reaction is stirred at −70° for 15 minutes and then allowed to warm to −25° where it is maintained for one hour. The solution is hydrolyzed by the addition of acetic acid (2 ml) and the solvent is removed to give a gum which is partitioned between ethyl acetate and water. The organic phase is washed with 5% $NaHCO_3$ and NaCl solution, dried, and evaporated to give t-butyl 7α-methoxy-7β-(p-nitrobenzyloxycarbonylamino)cephalosporanate.

The above product (4.32 g, 8 mmol) is dissolved in ethyl acetate (150 ml) and hydrogenated for 4 hours at 60 psi over 5% Pd on carbon. The reaction mixture is filtered and the filtrate is evaporated onto silica gel (16 g). Methylene chloride (150 ml) is added to the solid and the mixture is allowed to stand at room temperature for 1 hour. Additional silica gel (16 g) is added and the mixture is allowed to stand an additional two hours. The mixture is filtered and the silica gel is extracted with chloroform (3 × 150 ml). The combined organic phases are evaporated to give t-butyl 7α-methoxy-7β-aminocephalosporanate.

EXAMPLE 1 t-Butyl 7β-amino-7α-methoxy-3-(1-methyltetrazol-5-ylthiomethyl)-3-cephem-4-carboxylate (430 mg, 1.2 mmol), trifluoromethylmercaptoacetic acid (192 mg, 1.2 mmol) and dicyclohexylcarbodiimide (247 mg, 1.2 mmol) were dissolved in tetrahydrofuran and stirred for 1 hour. An additional 50 mg each of trifluoromethylmercaptoacetic acid and dicyclohexylcarbodiimide was added and the mixture allowed to stand overnight. The reaction was filtered and the filtrate was evaporated to give a residue which was dissolved in ethyl acetate and washed with dilute HCl, 5% $NaHCO_3$ and water. The organic layer was dried and evaporated to a residue which was chromatographed on silica gel with benzene and 10% acetone in benzene as eluant.

The t-butyl ester was dissolved in 1:1 trifluoroacetic acid:m-dimethoxybenzene (2 ml) and stirred for one hour at room temperature. The reaction was poured into ethyl acetate (50 ml) and extracted with 5% $NaHCO_3$. The aqueous phase was extracted with ether which was discarded. The aqueous phase was layered with ethyl acetate and acidified with 3N HCl to pH 1. Phases were separated and the aqueous layer reextracted with ethyl acetate. The combined ethyl acetate extracts were dried and evaporated to give 7α-methoxy-7β-trifluoromethylmercaptoacetamido-3-(1-methyltetrazol-5-ylthiomethyl)-3-cephem-4-carboxylic acid.

The acid was dissolved in ethyl acetate (10 ml) and 30% sodium 2-ethylhexanoate in isopropanol (200 mg) was added. Ether was added dropwise to precipitate the sodium salt which was collected.

EXAMPLE 2

When the products of Preparation 2 are acylated according to the procedure of Example 1, the following compounds are obtained:

7α-methoxy-7β-trifluoromethylmercaptoacetamidocephalosporanic acid
7α-methoxy-7β-trifluoromethylmercaptoacetamido-3-(5-methyl-1,3,4-thiadiazol-2-ylthiomethyl)-3-cephem-4-carboxylic acid
7α-methoxy-7β-trifluoromethylmercaptoacetamido-3-(5-methyl-1,3,4-oxadiazol-2-ylthiomethyl)-3-cephem-4-carboxylic acid
7α-methoxy-7β-trifluoromethylmercaptoacetamido-3-(1-methyl-1,2,3-triazol-5-ylthiomethyl)-3-cephem-4-carboxylic acid
7α-methoxy-7β-trifluoromethylmercaptoacetamido-3-(4-methyl-1,2,4-triazol-3-ylthiomethyl)-3-cephem-4-carboxylic acid
7α-methoxy-7β-trifluoromethylmercaptoacetamido-3-(4,5-dimethyl-1,2,4-triazol-3-ylthiomethyl)-3-cephem-4-carboxylic acid.

EXAMPLE 3

A solution of sodium 7α-methoxy-7β-trifluoromercaptoacetamidocephalosporanic acid (466 mg, 1 mmol), 4-mercapto-1,2,3-triazole (101 mg, 1 mmol), and sodium bicarbonate (84 mg, 1 mmol) in pH 6.4 phosphate buffer (50 ml) is stirred at 56° for 18 hours. The solution is acidified with 3N HCl to pH 2 and extracted with ethyl acetate. The extracts are dried and evaporated to give 7α-methoxy-7β-trifluoromethylmercaptoacetamido-3-(1,2,3-triazol-4-ylthiomethyl)-3-cephem-4-carboxylic acid.

When 3-mercapto-5-methyl-1,2,4-triazole is substituted into the above procedure 7α-methoxy-7β-trifluoromethylmercaptoacetamido-3-(5-methyl-1,2,4-triazol-3-ylthiomethyl)-3-cephem-4-carboxylic acid is obtained.

EXAMPLE 4

Reaction of trifluoromethylsulfinylacetic acid with t-butyl 7β-amino-7α-methoxy-3-(1-methyltetrazol-5-ylthiomethyl)-3-cephem-4-carboxylic acid according to the procedure of Example 1 gives 7α-methoxy-7β-trifluoromethylsulfinylacetamido-3-(1-methyltetrazol-5-ylthiomethyl)-3-cephem-4-carboxylic acid.

EXAMPLE 5

When the products of Preparation 2 are acylated according to the procedure of Example 4, the following compounds are obtained:

7α-methoxy-7β-trifluoromethylsulfinylacetamidocephalosporanic acid
7α-methoxy-7β-trifluoromethylsulfinylacetamido-3-(5-methyl-1,3,4-thiadiazol-2-ylthiomethyl)-3-cephem-4-carboxylic acid
7α-methoxy-7β-trifluoromethylsulfinylacetamido-3-(5-methyl-1,3,4-oxadiazol-2-ylthiomethyl)-3-cephem-4-carboxylic acid.
7α-methoxy-7β-trifluoromethylsulfinylacetamido-3-(1-methyl-1,2,3-triazol-5-ylthiomethyl)-3-cephem-4-carboxylic acid
7α-methoxy-7β-trifluoromethylsulfinylacetamido-3-(4-methyl-1,2,4-triazol-3-ylthiomethyl)-3-cephem-4-carboxylic acid
7α-methoxy-7β-trifluoromethylsulfinylacetamido-3-(4,5-dimethyl-1,2,4-triazol-3-ylthiomethyl)-3-cephem-4-carboxylic acid.

EXAMPLE 6

A solution of 7β-amino-7α-methoxy-3-(1-methyltetrazol-5-ylthiomethyl)-3-cephem-4-carboxylic acid in equal volumes of acetone and 3% sodium bicarbonate is cooled to −20° and treated dropwise with a solution of methylmercaptoacetyl chloride in acetone. The reaction is stirred 20 minutes at −15° and then allowed to warm to room temperature. The solution is washed with ether, layered with ethyl acetate and acidified to pH 3.5 with 3N HCl. The organic phase is separated and the aqueous phase is extracted with ethyl acetate. The combined ethyl acetate phases are dried and concentrated to give 7α-methoxy-7β-methylmercaptoacetamido-3-(1-methyltetrazol-5-ylthiomethyl)-3-cephem-4-carboxylic acid.

EXAMPLE 7

When the products of Preparation 2 are acylated according to the procedure of Example 6, the following compounds are obtained:

7α-methoxy-7β-methylmercaptoacetamidocephalosporanic acid
7α-methoxy-7β-methylmercaptoacetamido-3-(5-methyl-1,3,4-thiadiazol-2-ylthiomethyl)-3-cephem-4-carboxylic acid
7α-methoxy-7β-methylmercaptoacetamido-3-(5-methyl-1,3,4-oxadiazol-2-ylthiomethyl)-3-cephem-4-carboxylic acid
7α-methoxy-7β-methylmercaptoacetamido-3-(1-methyl-1,2,3-triazol-5-ylthiomethyl)-3-cephem-4-carboxylic acid
7α-methoxy-7β-methylmercaptoacetamido-3-(4-methyl-1,2,4-triazol-3-ylthiomethyl)-3-cephem-4-carboxylic acid
7α-methoxy-7β-methylmercaptoacetamido-3-(4,5-dimethyl-1,2,4-triazol-3-ylthiomethyl)-3-cephem-4-carboxylic acid.

EXAMPLE 8

Methylsulfinylacetic acid, t-butyl 7β-amino-7α-methoxy-3-(1-methyltetrazol-5-ylthiomethyl)-3-cephem-4-carboxylate, and dicyclohexylcarbodiimide are reacted together by the procedure of Example 1 to give 7α-methoxy-7β-methylsulfinylacetamido-3-(1-methyltetrazol-5-ylthiomethyl)-3-cephem-4-carboxylic acid.

EXAMPLE 9

When the products of Preparation 2 are acylated with methylsulfinylacetic acid according to the procedure of Example 1, the following compounds are obtained:

7α-methoxy-7β-methylsulfinylacetamidocephalosporanic acid
7α-methoxy-7β-methylsulfinylacetamido-3-(5-methyl-1,3,4-thiadiazol-2-ylthiomethyl)-3-cephem-4-carboxylic acid
7α-methoxy-7β-methylsulfinylacetamido-3-(5-methyl-1,3,4-oxadiazol-2-ylthiomethyl)-3-cephem-4-carboxylic acid
7α-methoxy-7β-methylsulfinylacetamido-3-(1-methyl-1,2,3-triazol-5-ylthiomethyl)-3-cephem-4-carboxylic acid 7α-methoxy-7β-methylsulfinylacetamido-3-(4-methyl-1,2,4-triazol-3-ylthiomethyl)-3-cephem-4-carboxylic acid 7α-methoxy-7β-methylsulfinylacetamido-3-(4,5-dimethyl-1,2,4-triazol-3-ylthiomethyl)-3-cephem-4-carboxylic acid.

EXAMPLE 10

Triethylamine is added to a suspension of 7β-amino-7α-methoxy-3-(1-methyltetrazol-5-ylthiomethyl)-3-cephem-4-carboxylic acid until all the solid is dissolved. An equivalent of N-hydroxysuccinimidyl methylsulfonylacetate is added and the solution is stirred at room temperature for 5 hours and then added dropwise to ether. The product is collected, dissolved in water containing triethylamine and then acidified to pH 2. The acidic aqueous solution is extracted with ethyl acetate which is dried and concentrated to a small volume which contains 7α-methoxy-7β-methylsulfonylacetamido-3-(1-methyltetrazol-5-ylthiomethyl)-3-cephem-4-carboxylic acid. The product is isolated as its sodium salt by addition of a solution of sodium 2-ethylhexanoate in isopropanol followed by ether. The precipitated salt is collected.

EXAMPLE 11

When the products of Preparation 2 are acylated according to the procedure of Example 10, the following compounds are obtained:

7α-methoxy-7β-methylsulfonylacetamidocephalosporanic acid

7α-methoxy-7β-methylsulfonylacetamido-3-(5-methyl-1,3,4-thiadiazol-2-ylthiomethyl)-3-cephem-4-carboxylic acid 7α-methoxy-7β-methylsulfonylacetamido-3-(5-methyl-1,3,4-oxadiazol-2-ylthiomethyl)-3-cephem-4-carboxylic acid 7α-methoxy-7β-methylsulfonylacetamido-3-(1-methyl-1,2,3-triazol-5-ylthiomethyl)-3-cephem-4-carboxylic acid 7α-methoxy-7β-methylsulfonylacetamido-3-(4-methyl-1,2,4-triazol-3-ylthiomethyl)-3-cephem-4-carboxylic acid 7α-methoxy-7β-methylsulfonylacetamido-3-(4,5-dimethyl-1,2,4-triazol-3-ylthiomethyl)-3-cephem-4-carboxylic acid.

EXAMPLE 12

By the same procedure as outlined in Example 10 7β-amino-7α-methoxy-3-(1-methyltetrazol-5-ylthiomethyl)-3-cephem-4-carboxylic acid is acylated with N-hydroxysuccinimidyl cyanomethylmercaptoacetate to give 7α-methoxy-7β-cyanomethylmercaptoacetamido-3-(1-methyltetrazol-5-ylthiomethyl)-3-cephem-4-carboxylic acid.

EXAMPLE 13

When the products of Preparation 2 are acylated according to the procedure of Example 12, the following compounds are obtained:

7α-methoxy-7β-cyanomethylmercaptoacetamidocephalosporanic acid

7α-methoxy-7β-cyanomethylmercaptoacetamido-3-(5-methyl-1,3,4-thiadiazol-2-ylthiomethyl)-3-cephem-4-carboxylic acid 7α-methoxy-7β-cyanomethylmercaptoacetamido-3-(5-methyl-1,3,4-oxadiazol-2-ylthiomethyl)-3-cephem-4-carboxylic acid 7α-methoxy-7β-cyanomethylmercaptoacetamido-3-(1-methyl-1,2,3-triazol-5-ylthiomethyl)-3-cephem-4-carboxylic acid 7α-methoxy-7β-cyanomethylmercaptoacetamido-3-(4-methyl-1,2,4-triazol-3-ylthiomethyl)-3-cephem-4-carboxylic acid 7α-methoxy-7β-cyanomethylmercaptoacetamido-3-(4,5-dimethyl-1,2,4-triazol-3-ylthiomethyl)-3-cephem-4-carboxylic acid.

EXAMPLE 14

When N-hydroxysuccinimidyl cyanomethylsulfinylacetate is substituted for N-hydroxysuccinimidyl cyanomethylmercaptoacetate into the procedure of Example 12, 7α-methoxy-7β-cyanomethylsulfinylacetamido-3-(1-methyltetrazol-5-ylthiomethyl)-3-cephem-4-carboxylic acid is obtained.

EXAMPLE 15

When the products of Preparation 2 are acylated according to the procedure of Example 14 the following compounds are obtained:

7α-methoxy-7β-cyanomethylsulfinylacetamidocephalosporanic acid

7α-methoxy-7β-cyanomethylsulfinylacetamido-3-(5-methyl-1,3,4-thiadiazol-2-ylthiomethyl)-3-cephem-4-carboxylic acid 7α-methoxy-7β-cyanomethylsulfinylacetamido-3-(5-methyl-1,3,4-oxadiazol-2-ylthiomethyl)-3-cephem-4-carboxylic acid 7α-methoxy-7β-cyanomethylsulfinylacetamido-3-(1-methyl-1,2,3-triazol-5-ylthiomethyl)-3-cephem-4-carboxylic acid 7α-methoxy-7β-cyanomethylsulfinylacetamido-3-(4-methyl-1,2,4-triazol-3-ylthiomethyl)-3-cephem-4-carboxylic acid 7α-methoxy-7β-cyanomethylsulfinylacetamido-3-(4,5-dimethyl-1,2,4-triazol-3-ylthiomethyl)-3-cephem-4-carboxylic acid.

EXAMPLE 16

When the 7β-aminocephem derivative of Example 6 is acylated with trifluoroethylmercaptoacetyl chloride by the analogous procedure outlined therein, 7α-methoxy-7β-trifluoroethylmercaptoacetamido-3-(1-methyltetrazol-5-ylthiomethyl)-3-cephem-4-carboxylic acid is obtained.

EXAMPLE 17

When the products of Preparation 2 are acylated according to the procedure of Example 16, the following compounds are obtained:

7α-methoxy-7β-trifluoroethylmercaptoacetamidocephalosporanic acid

7α-methoxy-7β-trifluoroethylmercaptoacetamido-3-(5-methyl-1,3,4-thiadiazol-2-ylthiomethyl)-3-cephem-4-carboxylic acid 7α-methoxy-7β-trifluoroethylmercaptoacetamido-3-(5-methyl-1,3,4-oxadiazol-2-ylthiomethyl)-3-cephem-4-carboxylic acid 7α-methoxy-7β-trifluoroethylmercaptoacetamido-3-(1-methyl-1,2,3-triazol-5-ylthiomethyl)-3-cephem-4-carboxylic acid 7α-methoxy-7β-trifluoroethylmercaptoacetamido-3-(4-methyl-1,2,4-triazol-3-ylthiomethyl)-3-cephem-4-carboxylic acid 7α-methoxy-7β-trifluoroethylmercaptoacetamido-3-(4,5-dimethyl-1,2,4-triazol-3-ylthiomethyl)-3-cephem-4-carboxylic acid.

EXAMPLE 18

When N-hydroxysuccinimidyl trifluoroethylsulfinylacetate is substituted for N-hydroxysuccinimidyl methylsulfonylacetate in the procedure of Example 10, 7α-methoxy-7β-trifluoroethylsulfinylacetamido-3-(1-methyltetrazol-5-ylthiomethyl)-3-cephem-4-carboxylic acid is obtained.

EXAMPLE 19

When the products of Preparation 2 are acylated according to the procedure of Example 18, the following compounds are obtained:

7α-methoxy-7β-trifluoroethylsulfinylacetamidocephalosporanic acid

7α-methoxy-7β-trifluoroethylsulfinylacetamido-3-(5-methyl-1,3,4-thiadiazol-2-ylthiomethyl)-3-cephem-4-carboxylic acid 7α-methoxy-7β-trifluoroethylsulfinylacetamido-3-(5-methyl-1,3,4-oxadiazol-2-ylthiomethyl)-3-cephem-4-carboxylic acid 7α-methoxy-7β-trifluoroethylsulfinylacetamido-3-(1-methyl-1,2,3-triazol-5-ylthiomethyl)-3-cephem-4-carboxylic acid 7α-methoxy-7β-trifluoroethylsulfinylacetamido-3-(4-methyl-1,2,4-triazol-3-ylthiomethyl)-3-cephem-4-carboxylic acid 7α-methoxy-7β-trifluoroethylsulfinylacetamido-3-(4,5-dimethyl-1,2,4-triazol-3-ylthiomethyl)-3-cephem-4-carboxylic acid.

EXAMPLE 20

When 7α-methoxy-7β-trifluoromethylsulfinylacetamidocephalosporanic acid, 7α-methoxy-7β-methylmercaptoacetamidocephalosporanic acid, 7α-methoxy-7β-methylsulfinylacetamidocephalosporanic acid, 7α-methoxy-7β-methylsulfonylacetamidocephalosporanic acid, 7α-methoxy-7β-cyanomethylmercaptoacetamidocephalosporanic acid, 7α-methoxy-7β-cyanomethylsulfinylacetamidocephalosporanic acid, 7α-methoxy-7β-trifluoroethylmercaptoacetamidocephalosporanic acid, and 7α-methoxy-7β-trifluoroethylsulfinylacetamidocephalosporanic acid are substituted for 7α-methoxy-7β-trifluoromethylmercaptoacetamidocephalosporanic acid in the procedure of Example 3 the following compounds are obtained:

7α-methoxy-7β-trifluoromethylsulfinylacetamido-3-(1,2,3-triazol-4-ylthiomethyl)-3-cephem-4-carboxylic acid 7α-methoxy-7β-methylmercaptoacetamido-3-(1,2,3-triazol-4-ylthiomethyl)-3-cephem-4-carboxylic acid 7α-methoxy-7β-methylsulfinylacetamido-3-(1,2,3-triazol-4-ylthiomethyl)-3-cephem-4-carboxylic acid 7α-methoxy-7β-methylsulfonylacetamido-3-(1,2,3-triazol-4-ylthiomethyl)-3-cephem-4-carboxylic acid 7α-methoxy-7β-cyanomethylmercaptoacetamido-3-(1,2,3-triazol-4-ylthiomethyl)-3-cephem-4-carboxylic acid 7α-methoxy-7β-cyanomethylsulfinylacetamido-3-(1,2,3-triazol-4-ylthiomethyl)-3-cephem-4-carboxylic acid 7α-methoxy-7β-trifluoroethylmercaptoacetamido-3-(1,2,3-triazol-4-ylthiomethyl)-3-cephem-4-carboxylic acid 7α-methoxy-7β-trifluoroethylsulfinylacetamido-3-(1,2,3-triazol-4-ylthiomethyl)-3-cephem-4-carboxylic acid.

EXAMPLE 21

An injectable pharmaceutical composition is prepared by dissolving 500 mg of sodium 7α-methoxy-7β-trifluoromethylmercaptoacetamido-3-(1-methyltetrazol-5-ylthiomethyl)-3-cephem-4-carboxylate in sterile water or sterile normal saline solution (1–2 ml). The other compounds within the scope of this invention including those described above are formulated in a similar manner.

An antibacterial capsule is comprised of the following components:

| | |
|---|---|
| cephalosporin | 500 mg |
| lactose | 250 mg |
| magnesium stearate | 75 mg |

We claim:
1. A compound of the formula

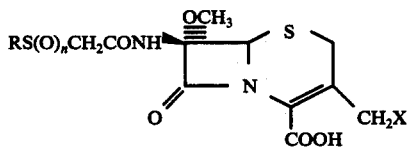

wherein
R is $CF_3$ or $CF_3CH_2$;
$n$ is 0, 1, or 2;
X is SHet; and
Het is tetrazolyl, triazolyl, thiadiazolyl, or oxadiazolyl, each unsubstituted or substituted with 1 or 2 alkyl groups of 1–4 carbon atoms,
or a pharmaceutically acceptable salt thereof.

2. A compound as claimed in claim 1 where Het is tetrazolyl, 1,2,4-triazolyl, 1,2,3-triazolyl, 1,3,4-thiadiazolyl, or 1,3,4-oxadiazolyl, each unsubstituted or substituted with 1 or 2 methyl groups.

3. A compound as claimed in claim 2 being the compound 7α-methoxy-7β-trifluoromethylmercaptoacetamido-3-(1-methyltetrazol-5-ylthiomethyl)-3-cephem-4-carboxylic acid.

4. A compound as claimed in claim 2 being the compound 7α-methoxy-7β-trifluoromethylmercaptoacetamido-3-(1,2,3-triazol-4-ylthiomethyl)-3-cephem-4-carboxylic acid.

5. A compound as calimed in claim 2 being the compound 7α-methoxy-7β-trifluoromethylmercaptoacetamido-3-(4-methyl-1,2,4-triazol-3-ylthiomethyl)-3-cephem-4-carboxylic acid.

6. A compound as claimed in claim 2 being the compound 7α-methoxy-7β-trifluoromethylmercaptoacetamido-3-(5-methyl-1,3,4-thiadiazol-2-ylthiomethyl)-3-cephem-4-carboxylic acid.

7. A compound as claimed in claim 2 being the compound 7α-methoxy-7β-trifluoromethylmercaptoacetamido-3-(5-methyl-1,3,4-oxadiazol-2-ylthiomethyl)-3-cephem-4-carboxylic acid.

8. A compound as claimed in claim 2 being the compound 7α-methoxy-7β-trifluoromethylsulfinylacetamido-3-(1-methyltetrazol-5-ylthiomethyl)-3-cephem-4-carboxylic acid.

9. A compound as claimed in claim 2 being the compound 7α-methoxy-7β-trifluoroethylmercaptoacetamido-3-(1-methyltetrazol-5-ylthiomethyl)-3-cephem-4-carboxylic acid.

10. A compound as claimed in claim 2 being the compound 7α-methoxy-7β-trifluoroethylsulfinylacetamido-3-(1-methyltetrazol-5-ylthiomethyl)-3-cephem-4-carboxylic acid.

* * * * *